United States Patent
Itsuji

(10) Patent No.: US 7,531,804 B2
(45) Date of Patent: May 12, 2009

(54) ANALYSIS APPARATUS AND ANALYSIS METHOD

(75) Inventor: Takeaki Itsuji, Hiratsuka (JP)

(73) Assignee: Canon Kabuhsiki Kaisha, Tokyo (JP)

( * ) Notice: Subject to any disclaimer, the term of this patent is extended or adjusted under 35 U.S.C. 154(b) by 0 days.

(21) Appl. No.: 11/935,180

(22) Filed: Nov. 5, 2007

(65) Prior Publication Data

US 2008/0210873 A1    Sep. 4, 2008

(30) Foreign Application Priority Data

Nov. 15, 2006    (JP)    .............................. 2006-308711

(51) Int. Cl.
    *G01N 21/00*    (2006.01)
(52) U.S. Cl. .................................. 250/341.1
(58) Field of Classification Search ............... 250/341.1
    See application file for complete search history.

(56) References Cited

U.S. PATENT DOCUMENTS

| | | | |
|---|---|---|---|
| 6,723,991 B1 * | 4/2004 | Sucha et al. ............. | 250/341.1 |
| 6,844,552 B2 * | 1/2005 | Zhang et al. ............. | 250/338.1 |
| 2002/0067480 A1 * | 6/2002 | Takahashi ................... | 356/317 |
| 2005/0162658 A1 * | 7/2005 | Pepper ....................... | 356/451 |
| 2007/0215810 A1 | 9/2007 | Kurosaka et al. .......... | 250/358.1 |
| 2007/0252992 A1 | 11/2007 | Itsuji ......................... | 356/369 |
| 2007/0279136 A1 | 12/2007 | Koyama et al. .......... | 331/107 T |
| 2007/0279143 A1 | 12/2007 | Itsuji ......................... | 331/185 |
| 2008/0048678 A1 | 2/2008 | Kurosaka et al. ............ | 324/639 |
| 2008/0116374 A1 | 5/2008 | Ouchi et al. ................ | 250/306 |

FOREIGN PATENT DOCUMENTS

| | | |
|---|---|---|
| EP | 828162 | 3/1998 |
| JP | 10-90174 | 4/1998 |
| JP | 2004-333344 | 11/2004 |

* cited by examiner

*Primary Examiner*—David P Porta
*Assistant Examiner*—Marcus H Taningco
(74) *Attorney, Agent, or Firm*—Fitzpatrick, Cella, Harper & Scinto

(57) ABSTRACT

An analysis apparatus and analysis method are provided for obtaining information on a sample from change in propagation state of a magnetic wave caused thereby, with less influence of frequency characteristics on the detection unit side. The analysis apparatus comprises a generating unit for generating a terahertz wave, a signal-making unit for making a code pattern, a delaying unit for delaying the code pattern produced by the signal-making unit, a band-diffusing unit for diffusing a band of the terahertz wave by modifying the phase of the terahertz wave generated by the generating unit in accordance with the code pattern produced by the signal-making unit, a detecting unit for detecting the terahertz wave, and a band-restoring unit for restoring the band by modulating the phase of the terahertz wave in accordance with the code pattern being output from the delaying unit before detection by the detecting unit.

11 Claims, 7 Drawing Sheets

TIME

TIME

ANALYSIS APPARATUS AND ANALYSIS METHOD

BACKGROUND OF THE INVENTION

1. Field of the Invention

The present invention relates to an analysis apparatus for obtaining information on a sample by an electromagnetic wave including an imaging apparatus, and relates also to a method of analysis with the apparatus.

2. Description of the Related Art

In recent years, various nondestructive inspection techniques have been developed which employ a high-frequency electromagnetic wave in a wavelength region from millimeter waves to terahertz waves (30 GHz to 30 THz; hereinafter referred to as a "terahertz wave").

The terahertz wave region covers absorption lines of various substances including biological molecules. The electromagnetic wave in this terahertz wavelength region is applicable to an imaging technique for safe perspective inspection in place of X-ray inspection, and useful also in a spectrometric technique for obtaining an absorption spectrum and a complex dielectric constant for examining a bonding state of molecules. Further, the electromagnetic wave in this wavelength range is promising for analysis of biological molecules, and estimation of a carrier concentration and mobility.

The above terahertz electromagnetic wave is applicable to nondestructive inspection and imaging which employ picosecond-order pulse signals as disclosed in Patent Document 1: Japanese Patent Application Laid-Open No. H10-090174. Further, a high-speed imaging technique is disclosed (Patent Document 2: Japanese Patent Application Laid-Open No. 2004-333344) in which the signal-making units are arrayed. In this technique, to prevent cross-talking between the signals produced by the plural signal-making units, the electromagnetic wave generated at the signal-making unit is coded, and the signals are diffused and transmitted according to a predetermined code pattern: the received signals are reproduced by electric correlation calculation based on a predetermined code pattern.

Such a signal diffusion technique is useful for higher confidentiality and higher SN ratio of signals.

SUMMARY OF THE INVENTION

The terahertz wave has a wavelength in the longest wavelength region of the electromagnetic wave obtainable by an optical device like a laser, and in the shortest wavelength region of the electromagnetic wave obtainable by an electronic device like a diode. Therefore, the detection/generation efficiency of the terahertz wave is low. For example, the terahertz waves obtained in Patent Document 1 give weak signals of a micro-watt order, and the detection sensitivity by the detector in the terahertz region is low.

As described above, the terahertz wavelength range is in a boundary region between the optical device-controllable region and the electronic device-controllable region. Therefore, the detection sensitivity of the detector in the terahertz wavelength region depends largely on the wavelength. When the diffused band signals are received and restored electrically, the transmitted signal can be restored incompletely owing to the wavelength dependency of the detector.

The present invention is directed to an analysis apparatus for obtaining information on a sample by utilizing a change in a propagation state of a terahertz wave, comprising: a generating unit for generating a terahertz wave, a signal-making unit for making a code pattern, a delaying unit for delaying the code pattern produced by the signal-making unit, a band-diffusing unit for diffusing a band of the terahertz wave by modifying the phase of the terahertz wave generated by the generating unit in accordance with the code pattern produced by the signal-making unit, a detecting unit for detecting the terahertz wave, and a band-restoring unit for restoring the band by modulating the phase of the terahertz wave in accordance with the code pattern being output from the delaying unit before detection by the detecting unit.

In the analysis apparatus, at least one pair of the band-diffusing unit and the generating unit, and at least one pair of the band-restoring unit and the detecting unit which pairs correspond to each other can be provided.

In the analysis apparatus, at least one of the band-diffusing unit and the band-restoring unit can vibrate mechanically the generating unit or the detecting unit in the direction of propagation of the terahertz to modulate the phase of the terahertz wave.

In the analysis apparatus, at least one of the band-diffusing unit and the band-restoring unit can control timing of generation or detection of the terahertz wave in the generating unit of the detecting unit by utilizing controlling light to modulate the phase of the terahertz wave. In the analysis apparatus, at least one of the band-diffusing unit and the band-restoring unit can have a delaying optical unit for controlling the incident timing of the control light for triggering the generation or detection of the terahertz wave in the generating unit or the detecting unit; and a vibrating unit for vibrating mechanically the delaying optical unit. In the analysis apparatus, at least one of the band-diffusing unit and the band-restoring unit can have a phase controller for controlling the phase of the terahertz wave propagating or the incident timing of the controlling light to the generating unit or the detecting unit. In the analysis apparatus, the apparatus can further comprise a chopper for modulating the intensity of the controlling light.

In the analysis apparatus, at least one of the band-diffusing unit and the band-restoring unit can control the phase of the propagating terahertz wave to modulate the phase of the terahertz wave.

The apparatus can further comprise a means for imaging characteristics of the sample by placing signals obtained in the detecting unit in the manner of making the signals correspond to points irradiated with the terahertz wave.

The present invention is directed to an analysis method for obtaining information on a sample by utilizing a change in propagation state of a terahertz wave, comprising the steps of: generating a terahertz wave, diffusing a band of the terahertz wave by modulating the phase of the terahertz wave in accordance with a code pattern, irradiating the sample with the terahertz wave having a diffused band obtained in the diffusing step, detecting the terahertz wave as a result of the irradiating step, band-restoring the band by modulating the phase of the terahertz wave before the detecting step in accordance with the code-pattern, and delaying the code-pattern to adjust the timing of restoration of the band in the band-restoring step.

The method can comprise further a step of imaging characteristics of the sample by placing signals obtained in the detecting step in the manner of making the signals correspond to points irradiated with the terahertz wave.

By the apparatus and method of the present invention, the phase of the terahertz wave is modulated according to a code pattern to diffuse the band, and the phase of the terahertz is modulated according to the code pattern before (or immediately before) the detection to restore the band.

Based on a signal detection principle independently of the detection characteristics of the detecting unit, the influence of the frequency characteristics of the detecting unit can be minimized in the restoration for more reliable signal detection and analysis. Further, the low efficiency of generation/detection of the terahertz wave can be improved by modulation of the phase of the terahertz wave by diffusion by the density and restoration of the phase for detection.

Further features of the present invention will become apparent from the following description of exemplary embodiments with reference to the attached drawings.

DESCRIPTION OF THE EMBODIMENTS

Figure 1:
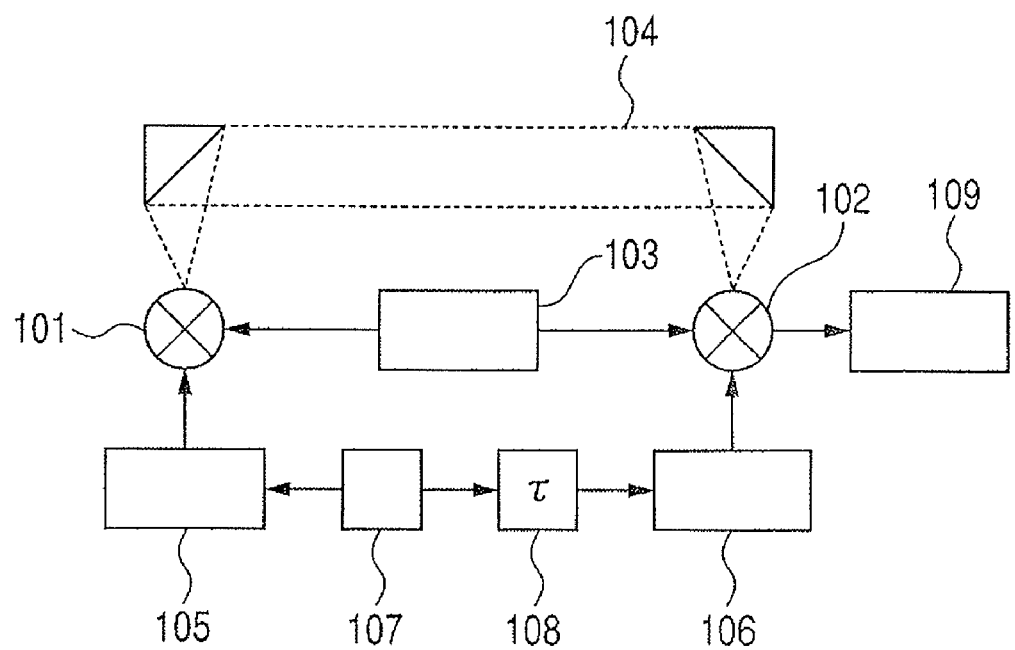
FIG. 1 illustrates schematically a constitution of an embodiment of the present invention.

The embodiments of the present invention are described with reference to drawings. In the drawings, the corresponding parts and members of the same function are denoted with the same symbols.

FIG. 1 illustrates schematically a constitution of an analysis apparatus and an analysis method of an embodiment of the present invention for obtaining information on a sample. This analysis apparatus comprises wave-generating unit 101, detecting unit 102, drive-controlling unit 103, wave-shaping unit 104, and processing unit 109. These units are collectively called a signal detection assembly for convenience. The analysis apparatus of this embodiment further comprises signal-processing assembly for diffusion and restoration, by a coding technique, of the high-frequency electromagnetic wave employed in the signal-detection assembly. This signal-processing assembly comprises band-diffusing unit 105, band-restoring unit 106, signal-making unit 107, and delaying unit 108.

The above-mentioned signal-detection assembly obtains information on a sample by employing high-frequency electromagnetic wave; specifically this assembly analyzes properties of the sample. Generating unit 101 of the signal-detection assembly generates the high-frequency electromagnetic wave employed for the analysis of the properties of the sample. In this embodiment, the terahertz wave is employed as the high-frequency electromagnetic wave. However, according to the principle of the signal detection of the present invention, the electromagnetic wave is not limited to the terahertz wave, but may be an electromagnetic wave of other wavelength region such as infrared light and visible light.

The system for the electromagnetic wave generation of generating unit 101 is not limited and may be any system which is capable of generating a terahertz wave. The useful system includes devices employing a current injection type of semiconductor element such as a quantum cascade laser and a resonance tunnel diode; oscillators employing a nonlinear optical crystal; oscillators employing an electron tube like a BWO (backward-wave oscillator); devices for switching optically with an antenna structure formed on a semiconductor substrate; and devices for generating terahertz waves by irradiation of laser onto a semiconductor substrate.

Detecting unit 102 detects the terahertz wave generated by generating unit 101. The system for detection is not limited insofar as the system can detect the terahertz wave. The useful system includes devices for switching optically with an antenna structure formed on a semiconductor substrate; thermal detectors such as a bolometer; devices utilizing an electro-optical effect; and devices employing a semiconductor element such as a Schottky diode.

Wave-shaping unit 104 shapes optically the terahertz wave generated by generating unit 101 and introduces the shaped wave into detecting unit 102. The terahertz wave has a certain rectilinear propagation property like an optical wave as well as penetrativeness like an electromagnetic wave. Therefore wave-shaping unit 104 may be constituted of an optical element such as a mirror and a lens.

In the inspection with the analysis apparatus of this embodiment, a sample is placed in the optical system constituted of wave-shaping unit 104, and a change in the terahertz wave propagation state caused by the sample is detected by detecting unit 102. When the sample is formless like a gas, the analysis can be conducted by placing the analysis system in a space containing the gas.

In FIG. 1, the optical system of wave-shaping unit 104 is illustrated as a parallel system, but may be constituted of a focusing system. Otherwise the optical system may contain a scanning mechanism (not illustrated in the drawing) for scanning the sample placed in the optical system. The apparatus can be also used as an imaging apparatus which scans the sample with the terahertz wave with the scanning mechanism. As described above, the constitution of wave-shaping unit 104 may be modified to meet the application of the inspection apparatus.

Drive-controlling unit 103 controls the driving system of generating unit 101 and detecting unit 102, including a control system for controlling the driving systems. For example, it gives a bias or projects an exciting light beam to generating unit 101 and detecting unit 102. Drive-controlling unit 103 may be modified depending on the constitution of generating unit 101 and detecting unit 102.

Processing unit 109 processes the signals of the terahertz wave detected by detecting unit 102 into a desired data format. For example, it measures spectrum of the sample, or measures the refractivity. When the inspection system of this embodiment is used as an imaging apparatus as mentioned above, processing unit 109 plots the processed data of the scanned points of the sample for imaging.

In the above description, the imaging apparatus employs a scanning mechanism for moving the sample for scanning but the scanning mechanism is not limited thereto. Otherwise the terahertz wave is allowed to scan the sample. Anyway the terahertz wave projected on the sample is allowed to scan relatively the sample.

In such a manner, the character of the sample can be imaged by arranging the signals detected by the scanning unit to correspond to the analysis points. Otherwise the character of the sample can be imaged with plural generating units and plural detecting units by arranging the signals detected by the plural detecting units to correspond to the analysis points.

The above-described signal-processing assembly is provided in addition to the signal detection assembly for analyzing the properties of the sample. This signal-processing assembly, for improving the detection sensitivity for the terahertz wave, diffuses and restores the terahertz wave by a coding technique by a mechanical means or a property-modulating means.

In this specification, the mechanical means serves to move mechanically a structure (e.g., an oscillator, and an optical system) to modulate the phase of the terahertz wave. The property-modulating means serves to change a property (e.g., refractive index), during propagation of the terahertz wave through a structure, to modulate the phase of the terahertz wave. Such a means is provided independently of the set of the control units (drive-controlling system, 103, etc.) relating directly to the control of generation and detection of the terahertz wave, and is not limited, insofar as it affects the propagation property of the terahertz wave.

Band-diffusing unit 105 of the signal-processing assembly controls the phase of the terahertz wave generated by generating unit 101 by means of a mechanical structure or the like. For example, generating unit 101 itself is allowed to vibrate mechanically at random to control the phase. In another way, a phase-delaying mechanism for the terahertz wave propagating from generating unit 101 is employed for controlling the phase. In still another way, the timing of generation of the terahertz wave in generating unit 101 is varied to control the phase. Thus the terahertz wave is allowed to propagate as a nearly random compressional wave.

Band-restoring unit 106 controls the phase of the terahertz wave introduced to detecting unit 102 by a mechanism similar to that of band-diffusing unit 105. Band-restoring unit 106 is placed between the sample and detecting unit 102: just before detecting unit 102, or just after the sample.

Signal-making unit 107 produces a control signal (diffusion signal) for the above phase-controlling mechanism constituting the band diffusion unit 105. The control signal causes diffusion of the band of the terahertz wave generated by generating unit 101 or propagating therefrom.

Further, the control signal produced by signal-making unit 107 is transmitted through delaying unit 108, and is utilized as a control signal (restoration signal) for a phase-controlling mechanism constituting the band-restoring unit 106. Delaying unit 108 controls the delay of the control signal introduced to band-restoring unit 106. In this embodiment, delaying unit 108 controls the delay of the control signal introduced to band-restoring unit 106, and estimates the correlation between the random compressional wave before arrival at detecting unit 102 and restoration signal controlled for delay to restore the signal before the diffusion. This restored signal is introduced to detecting unit 102 and is detected.

Figure 8A:
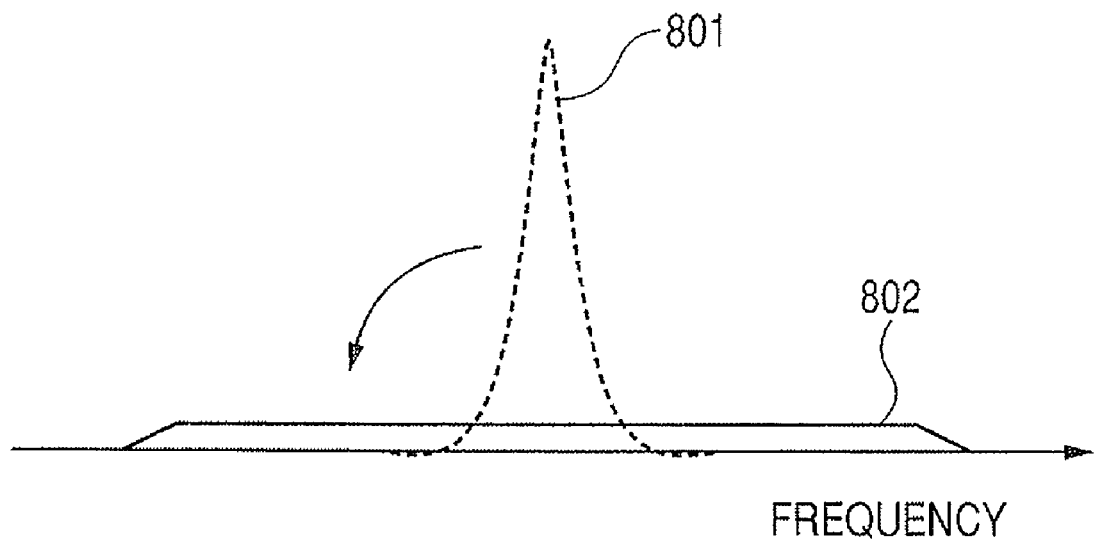
FIGS. 8A and 8B illustrate diffusion and restoration of the band.
Figure 8B:
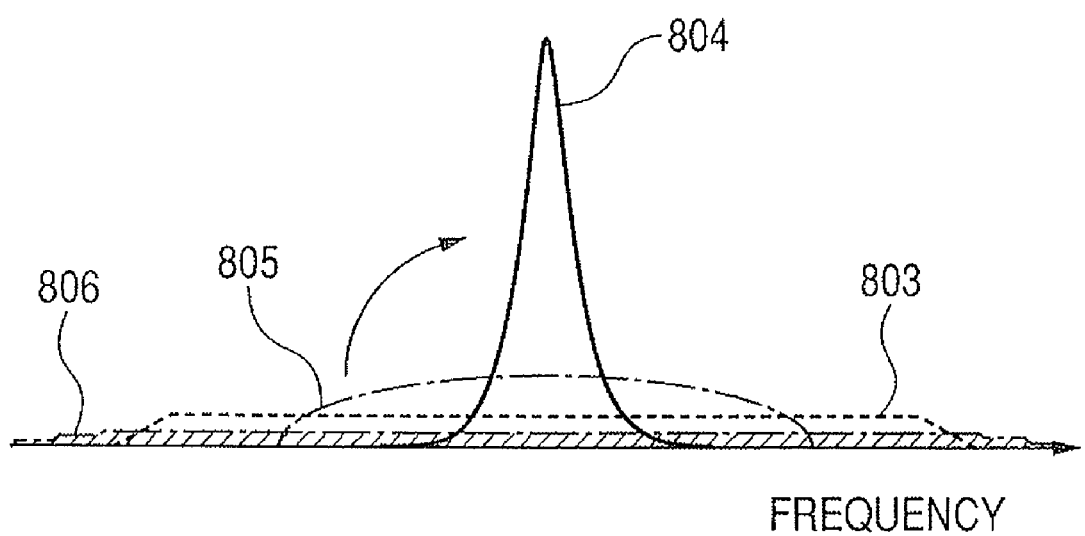

FIGS. 8A and 8B are imaging drawings for explaining the diffusion and restoration of the terahertz wave. FIG. 8A illustrates the operation for the diffusion, FIG. 8B illustrates the operation of restoration. In FIG. 8A, the frequency characteristics of the terahertz wave generated by generating unit 101 are equivalent to that of signal component 801 before the diffusion. The phase-controlling mechanism of band-diffusing unit 105 is controlled by random controlling signal (diffusion signal) produced by signal-making unit 107 to allow the terahertz wave to propagate as a random compressional wave. The characteristics of this compressional wave are equivalent to signal component 802 after the diffusion. As illustrated in FIG. 8A, signal component 802 after the diffusion has an intensity lower than that of signal component 801 before the diffusion at the respective wavelengths, but occupies a broader frequency bandwidth. This frequency bandwidth varies depending on the rate of change per unit time and randomness of the control signal employed for the diffusion.

In FIG. 8B, signal component 803 before the restoration is nearly equivalent to signal component 802 after the diffusion in FIG. 8A: not precisely equivalent because the signal component can be affected by the sample or an external noise. The diffused terahertz wave toward detecting unit 102 is treated by band-restoring unit 106 to be restored signal component 804.

More specifically, the signal produced by signal-making unit 107 for the band diffusion is delayed as intended by delaying unit 108. This delayed control signal (restoration signal) is utilized to control the phase-controlling mechanism of band-restoring unit 106 to detect the terahertz wave. For the detection, the correlation with the terahertz wave transmitted to detecting unit 102 is estimated from the control signal (restoration signal). If the correlation is insufficient (i.e., the delay is not suitable), the terahertz wave to be restored comes to be diffused again. Therefore, the delay extent caused by delaying unit 108 is adjusted by processing unit 109 so as to maximize the intensity of the terahertz wave detected by detecting unit 102.

In this embodiment, this controlled delay gives readily the phase change of the continuous wave or delay of the pulse wave.

The noise component, which has not been diffused by the control signal from signal-making unit 107, (noise component 805 before restoration shown by the one-dot chain line) diffuses without correlation in detection unit 102. Thereby, the band characteristic of noise component 805 before restoration diffuses as illustrated in FIG. 8B (noise component 806 after the restoration). Consequently, the SN ratio of the terahertz wave signal to the noise component reaching detection unit 102 is improved, whereby the detection sensitivity of the detecting unit 102 is improved.

In the above embodiment, the terahertz wave band is diffused and restored by generating unit 101 and detecting unit 102. However, the sites for the band diffusion and band restoration are not limited thereto. For example, the band restoration and band re-diffusion may be conducted before and after the sample in the terahertz wave propagation direction, whereby the interaction between the sample and the terahertz wave can be detected with high sensitivity and the high efficiency of the propagation.

In the above embodiment, the band of the terahertz wave is diffused and propagated to reduce influence of an external noise. If a noise-sensitive frequency component is present, the influence of the noise can be reduced relatively, since the band is diffused.

In the above embodiment, the signal transmission path of the signal detection assembly for detecting the signal and the signal transmission path of the signal processing assembly for processing for signal propagation with high efficiency and for detection with high sensitivity are separated to be independent. Thereby, the system can be constructed independently of the system characteristics (system frequency, frequency sensitivity dependency, etc.). This facilitates readily higher speed of the system.

According to the above embodiment, the effects below can be achieved.

In conventional techniques, the efficiency of the terahertz wave generation/detection is low, and detected terahertz wave is weak. Generally, for detection of such a weak signal, a weak signal detection technique is employed as in a lockin amplifier. However, this weak-signal detection technique, for higher signal detection sensitivity, a longer signal integration time is required. Application of a signal transmission technique disclosed in Patent Document 2 employing the diffusion technique limits the change rate of receivable diffusion signal per unit time owing to the long signal integration time. Specifically, it is difficult to detect the signal component changing at a high rate in a time shorter than the signal integration time of the detector. As the result, a longer measurement time is necessary owing to a longer time for obtaining the correlation of the received signals.

In contrast, in the above embodiment, the transmitted terahertz wave is diffused by compression, and the light quantity of the terahertz wave detected in a unit time by the detection unit is larger than that in a method of diffusion by ON-OFF of the electromagnetic wave. Therefore, in the above embodiment, the changing rate of receivable diffusion signal in a unit time is limited less, whereby the detection sensitivity is improved, the S/N ratio is improved, and the speed of the system is increased.

In conventional techniques, owing to wavelength dependency of the detector, a signal can exist in a wavelength range which cannot be supplemented to lower the light quantity of the terahertz wave detectable by the detector in a unit time to lower the detection sensitivity of the entire detection system. This problem can be reduced in the above embodiment.

For improvement of the detection sensitivity, an antenna is useful as disclosed in Patent Document 1. The frequency characteristics of the antenna can affect the sensitivity characteristics of the detector. This adverse effect can be reduced in the above embodiment.

In the above embodiment, the terahertz wave is diffused and restored by a mechanical means: specifically, the terahertz is generated or detected by an optical means or an electrical means of the signal detection assembly, whereas the signals are processed in a signal processing assembly employing a mechanical means. These assemblies are driven independently. Therefore the signal processing assembly can be constituted independently of the detection characteristics (such as frequency-sensitivity dependence and system frequency) of the detecting unit, enabling high speed detection with high confidentiality and without noise influence.

Further, in the above embodiment, the terahertz wave is diffused by modulation by mechanical means and the timing of the restoration is controlled by the delaying unit. Therefore, from this timing information (i.e., delay time), the phase shift of the terahertz wave can be achieved simultaneously. This phase shift can be achieved for a continuous wave, which is difficult by conventional terahertz wave detection system, to obtain the phase information. Further, in the case of a pulse wave, the delay state of the pulse wave can be judged instantaneously.

The system of the above embodiment, which diffuses and propagates the terahertz wave, enables detection with high propagation efficiency without influence of the atmospheric air, even in the presence of moisture.

EXAMPLES

Examples of the present invention are described specifically with reference to drawings.

Example 1

This Example describes specifically the apparatus and method of the analysis described above. Incidentally, the same descriptions as that mentioned above are omitted.

Figure 2:
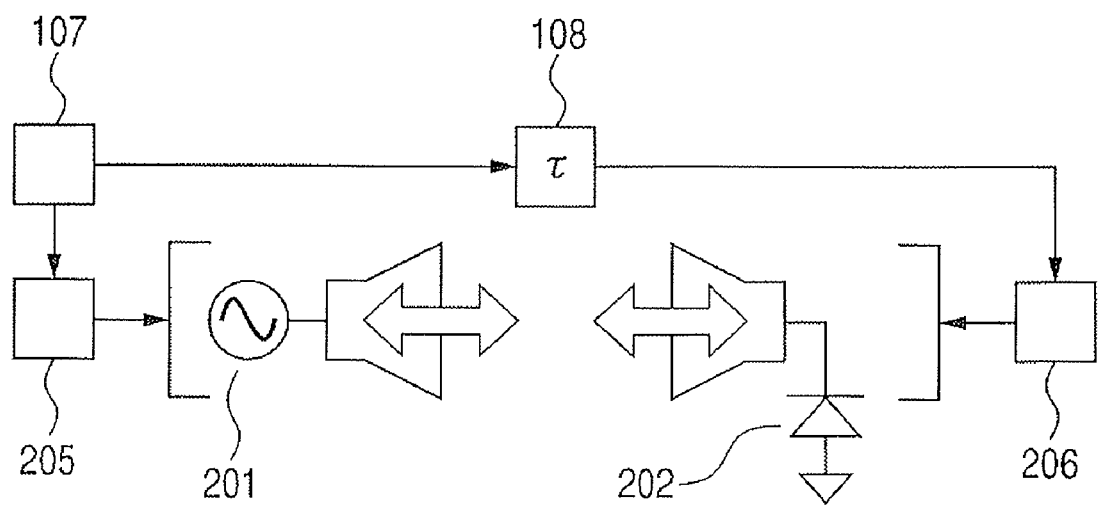
FIG. 2 illustrates schematically a constitution of Example 1 of the present invention.

FIG. 2 illustrates schematically a constitution of the analysis apparatus of this Example. As illustrated in FIG. 2, vibrating unit 205 is employed as band-diffusing unit 105; vibrating unit 206 is employed as band-restoring unit 106; oscillator 201 for emitting a terahertz wave of a simple frequency component is employed as generating unit 101; and detector 202 having sufficient sensitivity for detection of the terahertz wave from oscillator 201 is employed as detecting unit 102.

A frequency multiplier which utilizes nonlinearity of a semiconductor element is employed as oscillator 201 which emits a simple-frequency terahertz wave. However, the oscillator is not limited thereto. The oscillator includes semiconductor elements like a quantum cascade laser and a resonance tunnel diode; oscillators utilizing a nonlinear optical crystal; oscillators employing an electronic tube like a BWO. Any type of oscillator 201 may be employed which is capable of emitting a simple frequency wave. Such an oscillator can readily be miniaturized, and is capable of emitting a coherent electromagnetic wave of relatively high power. The phase state of the coherent electromagnetic wave is readily controllable, and the change of the phase is readily detectable.

The above oscillator 202 employs a Schottky diode, but is not limited thereto. The oscillator may employ another semiconductor element, a thermal detector like a bolometer, or an electro-optical device. Detector 202 is not limited in its type, insofar as it is capable of detecting the terahertz wave emitted from oscillator 201.

Drive-controlling unit 103, which is not shown in FIG. 2, may be any system like a power source which is capable of driving oscillator 201 and detector 202.

Vibrating unit 205 and vibrating unit 206 are respectively an actuator for vibrating oscillator 201 and detector 202. The actuator may be a piezo-actuator, but is not limited thereto. Signal-making unit 107 and delaying unit 108 are respectively drives vibrating unit 205 and vibrating unit 206. The type of signal-making unit 107 and the type of delaying unit 108 are selected to be suitable for the driving system of vibrating unit 205 and vibrating unit 206. Signal-making unit 107 outputs control signals nearly randomly in time. Vibrating unit 205 is driven by the control signal to vibrate oscillator 201 in the direction of propagation of the terahertz wave. Further, the control signal produced by signal-making unit 107 is transmitted through delaying unit 108 to drive vibrating unit 206. Vibrating unit 206 vibrates detector 202 in the propagation direction of the terahertz wave.

Oscillator 201 and detector 202 are moved to-and-fro in the direction of the terahertz wave propagation respectively by vibrating unit 205 and vibrating unit 206. In the movement, the pattern of the movement is controlled by the above control signal nearly randomly in time. Taking the reference positions at the neutral positions of oscillator 201 and detector 202, the distances of the movement of oscillator 201 and detector 202 are not limited, but is preferably about an interval between peaks of the terahertz wave (from $\pi$ to $-\pi$ in terms of the phase), namely one wave length.

Figure 9:
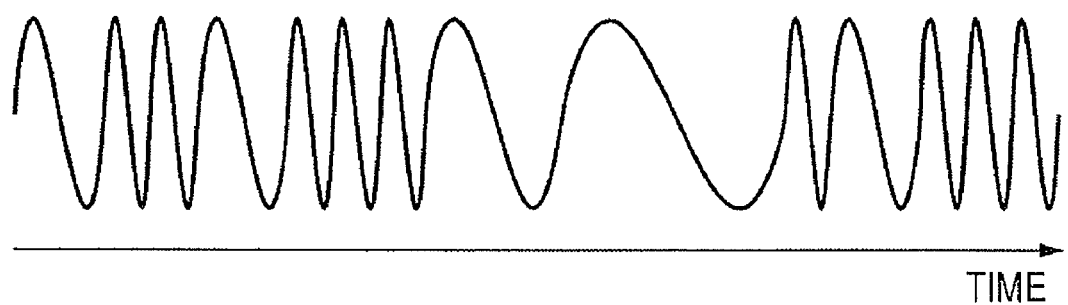
FIG. 9 illustrates diffusion of a band of a continuous wave.

FIG. 9 illustrates an example of the waveform of the terahertz wave generated by oscillator 201 of such a constitution. The vibration of oscillator 201 in the propagation direction of the terahertz wave forms an intensity-compressional wave as illustrated in FIG. 9. In the present invention, the term "compressional wave" signifies a wave having a waveform obtained by modulation of the frequency or phase of the generated terahertz wave. In this Example, the compression of the terahertz wave diffuses the bandwidth of the terahertz wave. The extent of this diffusion depends on the density of the compressional wave and the randomness of the compression pattern.

Detector 202 functions to cancel the compression state of the terahertz wave. Specifically, vibrating unit 206 controls the position of detector 202 in the direction of propagation of the terahertz wave. For example, when a non-compressed portion of the terahertz wave is reaching the detector 202, detector 202 is displaced to come near to oscillator 201: when a compressed portion of the terahertz wave is reaching the detector 202, detector 202 is displaced to be distant from oscillator 201. In such a position control, the compression interval is uniformized (corresponding to the band restoration). The terahertz wave having the restored band is detected by detector 202.

The compression pattern of the terahertz wave is nearly random corresponding to the control signal from signal-making unit 107 with respect to time. For example, when the position control pattern is different from the wave compression pattern, the terahertz wave band is diffused further in the portion of detector 202 to form a more random compressional wave and to decrease the intensity of the intended frequency component. In some cases, the detection of the signal can become difficult. To avoid this, in this Example, the control signal for vibrating unit 206 at the side of detector 202 is made to be the same as that control signal for vibrating unit 205 at the side of oscillator 201. The control timing of this control signal is adjusted by delaying unit 108. If the timings for the vibrating units are different for the control patterns, the compression pattern cannot be restored even with the same control pattern.

The adjustment of timing of the control by delaying unit 108 is conducted, for example, in FIG. 2 by processing unit 109 (not shown in the drawing) by monitoring the intensity of the intended frequency component of the output from detector 202. More specifically, the timing of the delay of the control signal in delaying unit 108 is adjusted to maximize the intensity of the frequency component monitored by processing unit 109. This timing control corresponds to detection of phase shift of the transmitted terahertz wave. Therefore, as described above, the phase shift caused by a sample placed in the propagation path of the terahertz wave can be detected.

The above-mentioned control enables diffusion and restoration of the terahertz wave band, and high efficiency of transmission of the signal. Further the adjusted signals in delaying unit 108 facilitate catching of the signal of the phase shift of the terahertz wave which may be of a continuous wave. In such a manner, the phase shift of the signals transmitted in a high efficiency gives information on the properties of a sample placed in the propagation path, regarding identification, property measurement, imaging, and so forth.

In the above constitution, both the generating unit and the detecting unit are vibrated mechanically in the terahertz wave propagation direction. Otherwise, one of the two units may be vibrated.

Example 2

This Example describes another embodiment of the analysis apparatus of the present invention, specifically a modification of Example 1 regarding the band diffusion and band restoration of the terahertz wave. In the description below, the matters common to the above description are omitted.

Figure 3A:
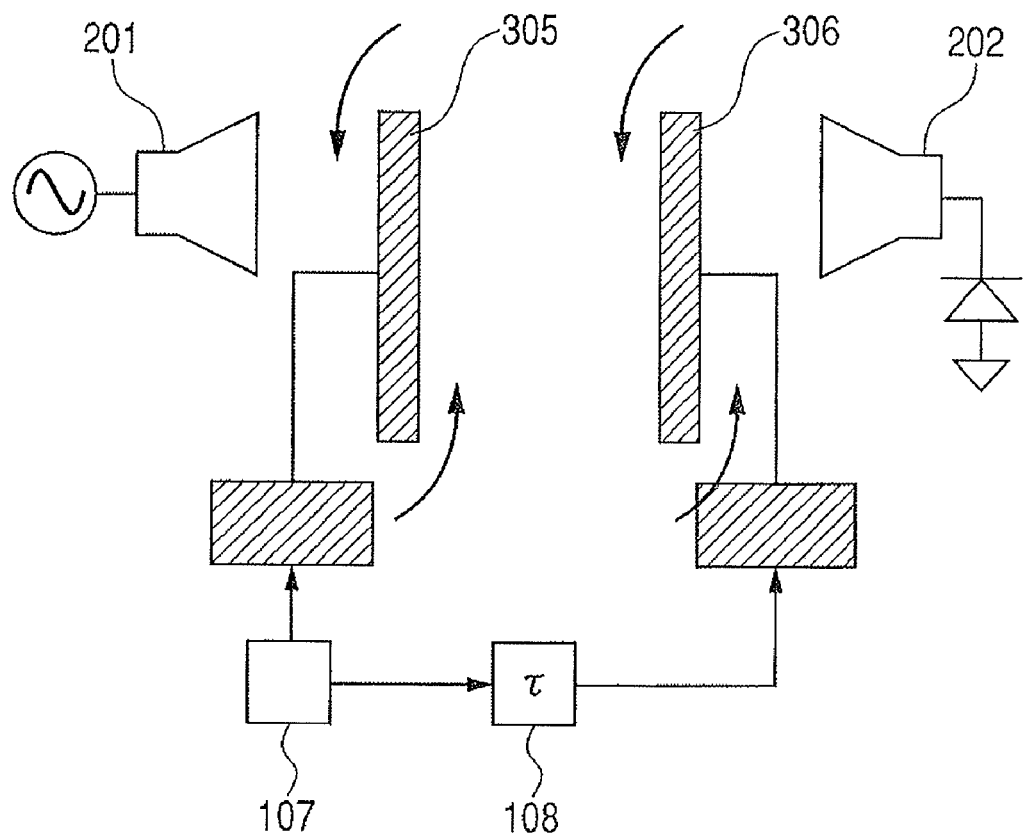
FIGS. 3A, 3B and 3C illustrate schematically a constitution of Example 2 of the present invention.
Figure 3B:
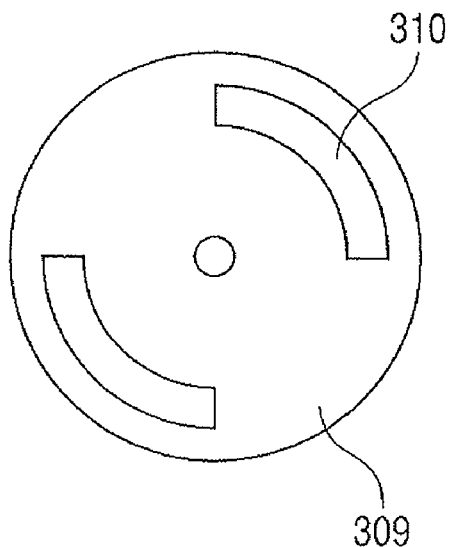
Figure 3C:
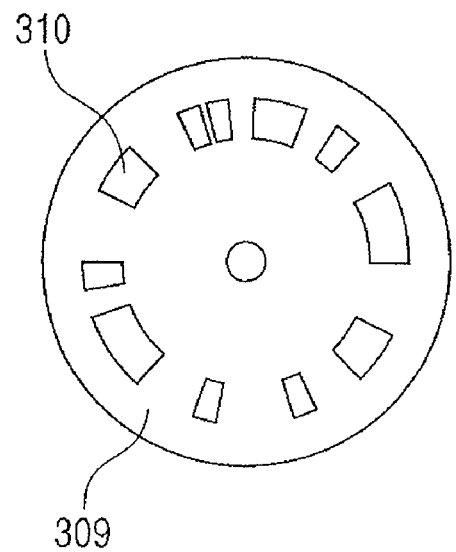

FIGS. 3A, 3B, and 3C illustrate schematically a constitution of the apparatus and method of the analysis of this Example. FIG. 3A illustrates the entire constitution; and FIGS. 3B and 3C illustrate respectively the constitution of the band diffusion portion and the band restoration portion. In this Example, phase controller 305 is employed as band diffusing unit 105, and phase controller 306 is employed as band restoring unit 106. This Example is different from Example 1 in that band-diffusing unit 105 and band-restoring unit 106 are placed respectively outside oscillator 201 and detector 202.

Phase controller 305 and phase controller 306 have respectively a rotating disk 309 having phase-modulating part 310, and a mechanism for driving this rotating disk 309. Phase-modulating parts 310 are placed on the peripheral portion of rotating disk 309 periodically at equiangular intervals as illustrated in FIG. 3B, or randomly and discontinuously on the peripheral portion of rotating disk 309 as shown in FIG. 3C. The former phase-modulating part is constituted of a rotating disk having periodically phase-modulating parts, whereas the latter phase-modulating part is constituted of a rotating disk having a phase-modulating part placed in a pattern corresponding to a code pattern.

The terahertz wave emitted from oscillator 201 propagates through the peripheral portion of rotating disk 309 containing a phase-modulating part 310. Phase controller 305, phase controller 306, and phase-modulating part 310 are formed from a terahertz-wave-transmitting material. The terahertz wave transmitted through phase-modulating part 310 has a phase state different from that of the terahertz wave transmitting through the part other than phase-modulating part 310, having an advanced phase state or a delayed phase state.

In one method for conducting such an operation, phase-modulating part 310 of phase controller 305 is constituted of a material having a refractive index different from that of rotating disk 309. For example, rotating disk 309 is constituted of a high-resistance silicon and phase-modulating part 310 is constituted of quartz. However, the materials are not limited thereto, insofar as the refractive index of phase-modulating part 310 is different from that of rotating disk 309. Preferably the both material are transparent to the employed terahertz wave.

In this Example, rotating disk 309 is constituted of a terahertz wave-transmissive member, but is not limited thereto. For example, only the peripheral portion is constituted of a terahertz wave-transmissive material and the main portion of the rotating disk may be constituted of non-transmissive material like a metal. For example, plural windows are provided on the peripheral portion for transmission of the terahertz wave, and in the windows plural kinds of phase-modulating parts 310 are arranged. The phase of the terahertz wave can be modulated by changing the thickness of the material in wave transmission direction, not only the change of the refractive index of the material of phase-modulating parts 310.

To prevent reflection by the rotating disk, the surface of the rotating disk may be covered with non-reflection coating, or is formed in a sub-wavelength structure (SWS).

With the rotating disk having phase-modulating parts 310 periodically as illustrated in FIG. 3B, the signal-making unit 107 controls phase controller 305 and phase controller 306 to obtain random rotation speed. With a random arrangement of phase-modulating part 310 as illustrated in FIG. 3C, signal-making unit 107 allows phase-controller 305 and phase controller 306 to rotate at a constant rotation speed, or at a randomly changing rotation speed.

In this Example, the phase of the transmitted terahertz wave is controlled outside oscillator 201 and detector 202 to generate compressional wave of the terahertz wave as illustrated in FIG. 9, and the band of the terahertz wave is diffused and restored. In this Example, employing rotation type of band diffusing unit 105 and band-restoring unit 106, enables diffusion and restoration at a high speed. Thereby the density of the compressional wave can be increased readily with a high efficiency of the transmission.

In the above constitution, mechanical phase-controllers are employed for both of the band-diffusing unit and the band-restoring unit to control mechanically the phase states. However, the phase controller may be used for only one thereof.

Example 3

This Example describes still another embodiment of the analysis apparatus of the present invention, specifically a modification of Example 1 regarding the band of the employed terahertz wave. In the description below, the matters common to the above description are omitted also.

Figure 4:
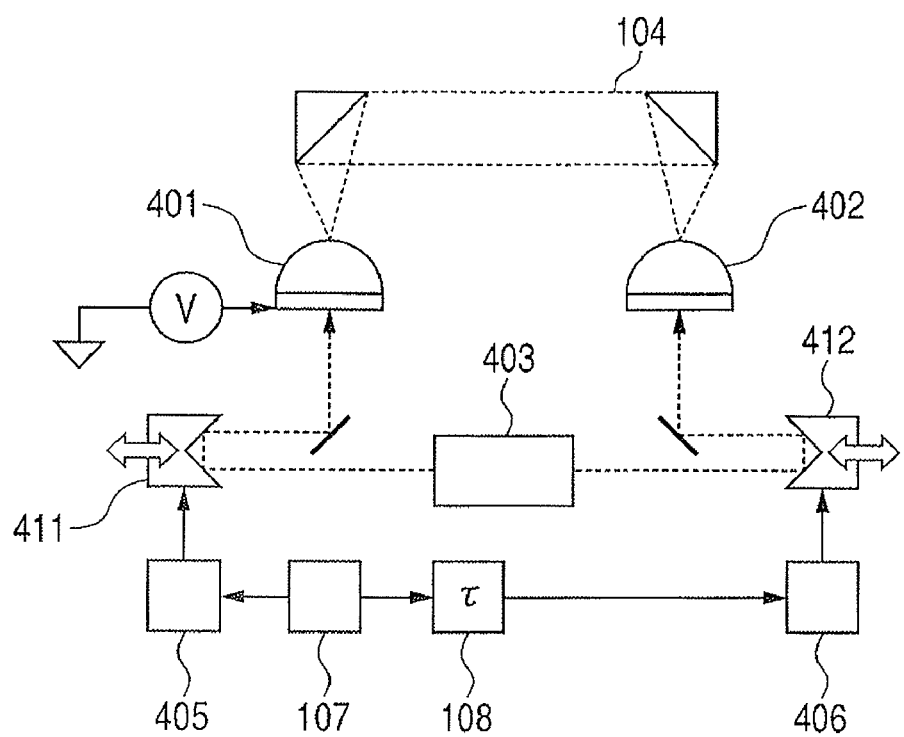
FIG. 4 illustrates schematically a constitution of Example 3 of the present invention.

FIG. 4 illustrates schematically a constitution of the apparatus and method of the analysis of this Example. In this Example, generating element 401 is employed as generating unit 101; detecting element 402 is employed as detecting unit 102; and a pulsed terahertz wave is employed differently from the above Examples in which the terahertz wave is a continuous wave.

In this Example, generating element 401 and detecting element 402 have respectively an antenna structure formed on a semiconductor substrate. The semiconductor substrate is a GaAs substrate of 100 μm thick having on the surface an LT-GaAs epitaxial growth layer of 1.5 μm thick. The antenna structure is a dipole antenna structure having a gap of 5 μm at the center. This antenna of the dipole antenna structure is formed from gold (AuGe/Ni/Au) having a length of 30 μm, and is formed by a conventional vapor deposition process. The antenna structure is not limited thereto. The size and form of the antenna depend on the frequency characteristics of the electromagnetic wave to be employed. The material of the semiconductor substrate is not limited to that mentioned above.

With the generating element 401 of the above antenna structure, a bias is applied to the gap of the antenna and the gap is utilized as an optical gate by use of an ultrashort pulsed light of femtosecond order, and the generated electromagnetic wave is utilized as the terahertz wave. The method of generation of the terahertz wave is not limited thereto. A pulsed light having a difference-frequency of two laser beams of different laser wavelength may be used for the gating.

With the detecting element 402 of the antenna structure, the gap is utilized as the optical gate by utilizing a femtosecond order of ultrashort pulsed wave. The variation of the carriers caused by the electromagnetic field of the terahertz wave is detected as an electric current. The method of the detection is not limited thereto.

In this Example, a pulsed laser beam source 403 emitting the ultrashort pulsed light is employed as drive-controlling unit 103 for control of generating element 401 and detecting element 402. Pulse laser light source 403 generates periodically the ultrashort pulsed light. Thereby generating element 401 generates a terahertz wave periodically invariably. The abovementioned semiconductor substrate is selected depending on the wavelength of this laser light.

As described above, for detecting the transmitted terahertz wave, the ultrashort pulsed light should be projected at the same time as arrival of the terahertz wave at detection element 402. This timing of projection of the ultrashort pulsed light is controlled two delaying optical units 411, 412. Specifically, by utilizing the optical path difference between delaying optical unit 411 and delaying optical unit 412, the timings of projection of ultrashort pulsed light to generating element 401 and detecting element 402 are made different to control the projection timing of the projection of the ultrashort pulsed light to the detecting element 402.

Figure 10:
FIG. 10 illustrates diffusion of a band of a pulse wave.

In this Example, vibrating unit 405 is employed for vibration of delaying optical unit 411 as band-diffusing unit 105, and vibrating unit 406 is employed for vibration of delaying optical unit 412 as band-restoring unit 106. The vibration patterns of vibrating units 405, 406 are controlled by signal-making unit 107 similarly as in the above Examples. In this Example, vibrating unit 405 vibrates delaying optical unit 411 to change the projection timing of the ultrashort pulsed light to generating element 401 nearly randomly. Consequently, the timing of generation of the terahertz wave by generating element 401 is varied nearly randomly as shown in FIG. 10. Generally, a pulsed wave can be represented as assemblage of innumerable continuous waves. The random change of the generation timing corresponds to diffusion of the band of the continuous waves.

The movement distances of vibrating unit 405 and vibrating unit 406 are not limited. However, preferably the movement distance is selected to be within the interval of the adjacent ultrashort pulsed light emitted from pulse laser light source 403.

In this Example, similar to the above Examples, vibrating unit 406 is controlled, to keep constant the timing of introduction of randomly transmitted terahertz wave (pulsed wave) to detecting element 402 (corresponding to band restoration), and the terahertz wave of restored band is detected. With this constitution, the principle of the present invention is applicable to a system employing a pulsed terahertz wave.

In this Example, both the band-diffusing unit and the band-restoring unit employ respectively the delaying optical unit for controlling the timing of introduction of control light (the above ultrashort pulsed light) for triggering the terahertz wave generation in the generating unit and detection of the terahertz wave in the detecting unit; and the vibrating unit for vibrating mechanically the delaying optical unit. However, such a constitution may be employed in one of the band-diffusion unit and the band-restoring unit.

Example 4

This Example is a modification of Example 3. In the description below, the matters common to the above description are omitted.

In the above Example 3, the terahertz wave pulse generated by generating element 401 is detected in real time by detecting element 402. However, in some cases, the real-time detection can be not easy depending on the frequency characteristics of the terahertz wave employed. The constitution of this Example is applicable to such a case.

Figure 5:
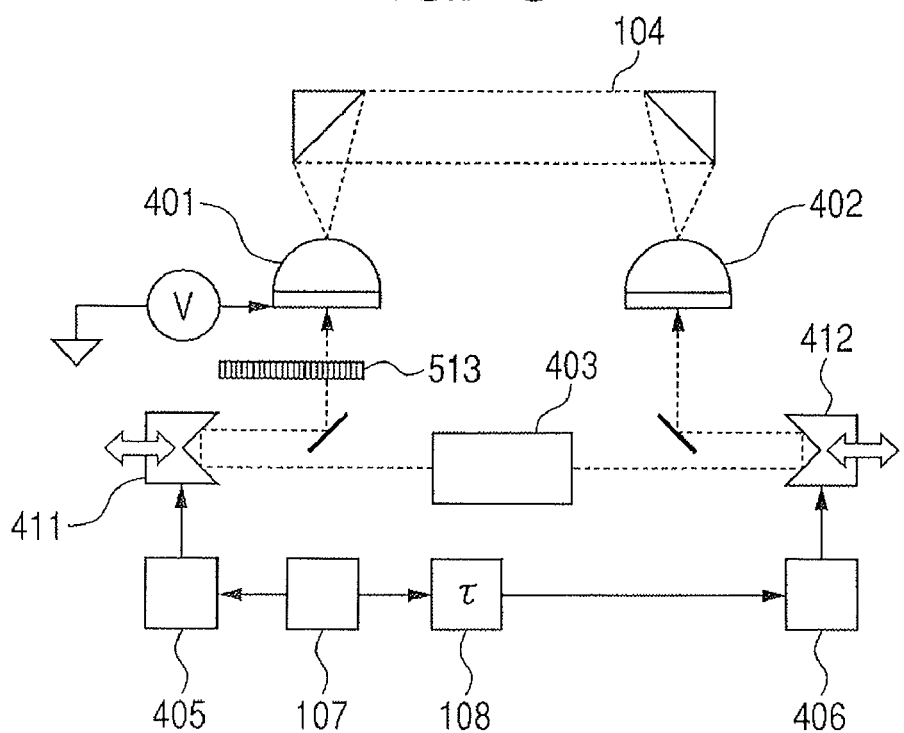
FIG. 5 illustrates schematically a constitution of Example 4 of the present invention.

FIG. 5 illustrates schematically a constitution of the apparatus and method for the analysis of this Example. In this Example, chopper 513 is employed, which is different from Example 3. Chopper 513 modulates the intensity of the controlling light, namely the amplitude of the ultrashort pulse light, introduced to generating element 401 at the chopping frequency. Thereby, the amplitude of the terahertz wave pulse generated by generating element 401 is modulated by the chopping frequency.

In this Example employing chopper 513, an amplifier like a lockin amplifier is connected to detecting element 402. As described in Example 3, the ultrashort pulsed light gates optically the gap of the antenna constituting detecting element 402. The lockin amplifier detects optically the signal just gated. In this detection, the intensity is detected at an arbitrary point of the terahertz wave which is just gated by the ultrashort pulsed light. For this purpose, the timing of the gating is swept by delaying optical unit 412 to obtain the terahertz wave in the time domain. This corresponds to sampling of terahertz wave by the ultrashort pulse light. This method is called a terahertz time domain spectroscopy (THz-TDS).

In this Example, the band is diffused and restored for the respective sampling points by controlling the timing of introduction of the ultrashort pulsed light to generating element 401 and detecting element 402 by utilizing vibrating unit 405 and vibrating unit 406.

As described above, in this Example, the signal is detected through diffusion and restoration of the band by THz-TDS. Specifically, the band is diffused and restored at sampling points of the terahertz wave modulated by the chopping frequency. Therefore, the frequency characteristics of the signal for diffusion of the band and the frequency characteristics of the chopping frequency are readily brought close. This facilitates diffusion and restoration of the band in a broader band region, and enables signal transmission at a higher efficiency with high confidentiality.

Example 5

This Example is a modification of Example 3 which conducts diffusion and restoration of the band of the employed terahertz wave. In the description below, the matters common to the above description are omitted.

Figure 6A:
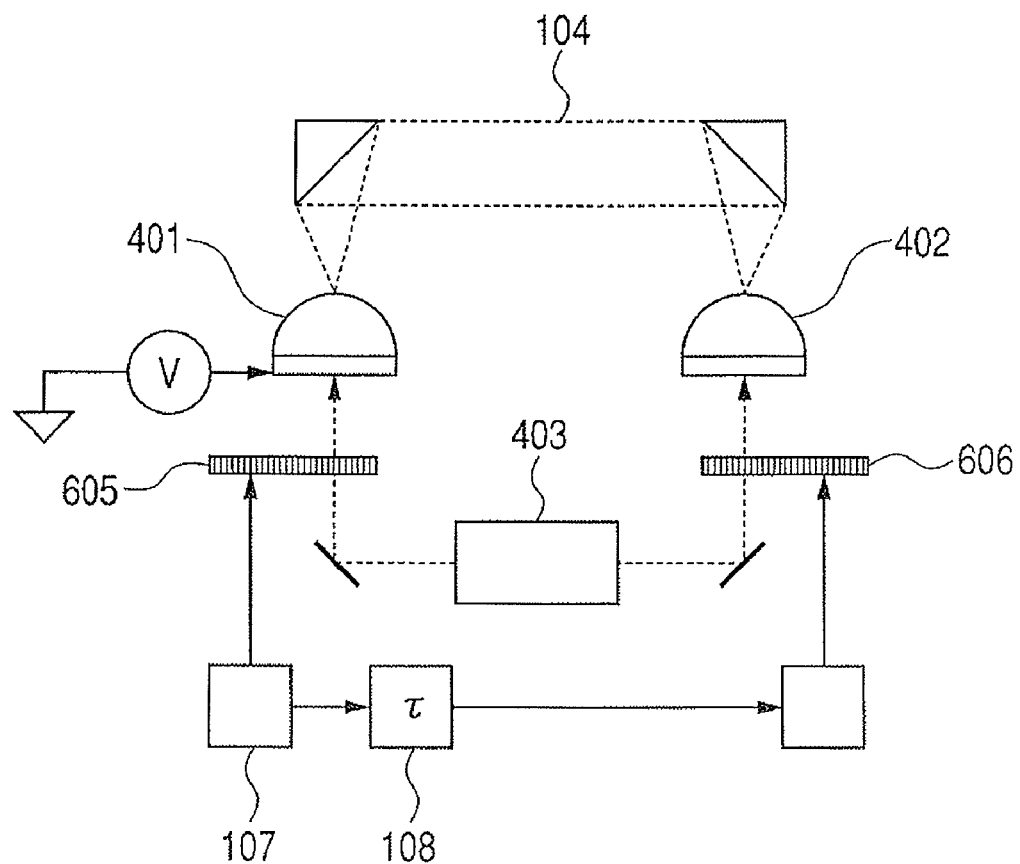
FIGS. 6A, 6B and 6C illustrate schematically a constitution of Example 5 of the present invention.
Figure 6B:
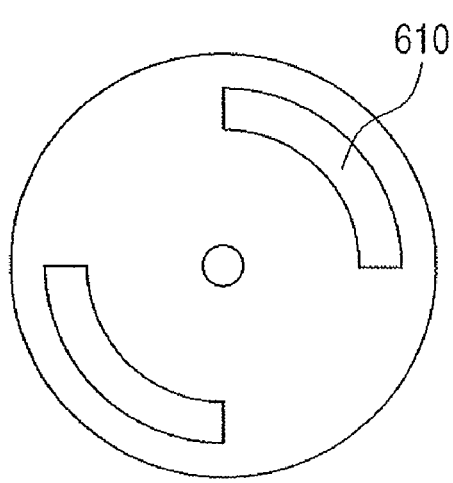
Figure 6C:
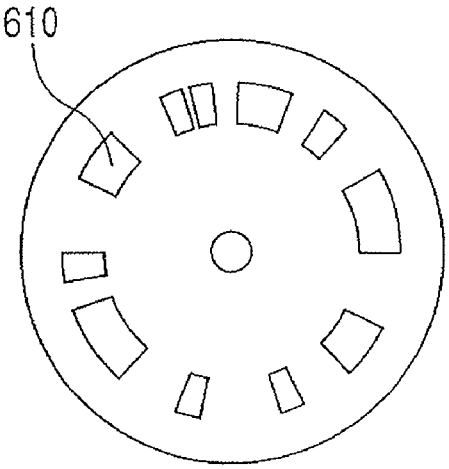

FIGS. 6A, 6B, and 6C illustrate schematically a constitution of the apparatus and method of the analysis of this Example. FIG. 6A illustrates the entire constitution; FIGS. 6B and 6C illustrate respectively the constitution of the band diffusion portion and the band restoration portion. In this Example, phase controller 605 is employed as band diffusing unit 105, and phase controller 606 is employed as band restoring unit 106.

Phase controllers 605, 606 have the same constitution as that of phase controllers 305, 306 described in Example 2. Therefore the explanation thereof is omitted. Phase controllers 605, 606 in this Example control the phase of ultrashort pulsed light, whereas phase controllers 305, 306 in Example 2 control the phase of a terahertz wave. Therefore phase-modulating parts 610 are transparent to the ultrashort pulsed light.

In this Example, phase controllers 605, 606 control respectively the timing of introduction of the ultrashort pulsed light to generating element 401 and detecting element 402. Thereby the terahertz wave pulse band is diffused and restored.

Example 6

This Example is a modification of Example 4 which conducts diffusion and restoration of the band of the employed terahertz wave. In the description below, the matters common to the above description are omitted.

Figure 7:
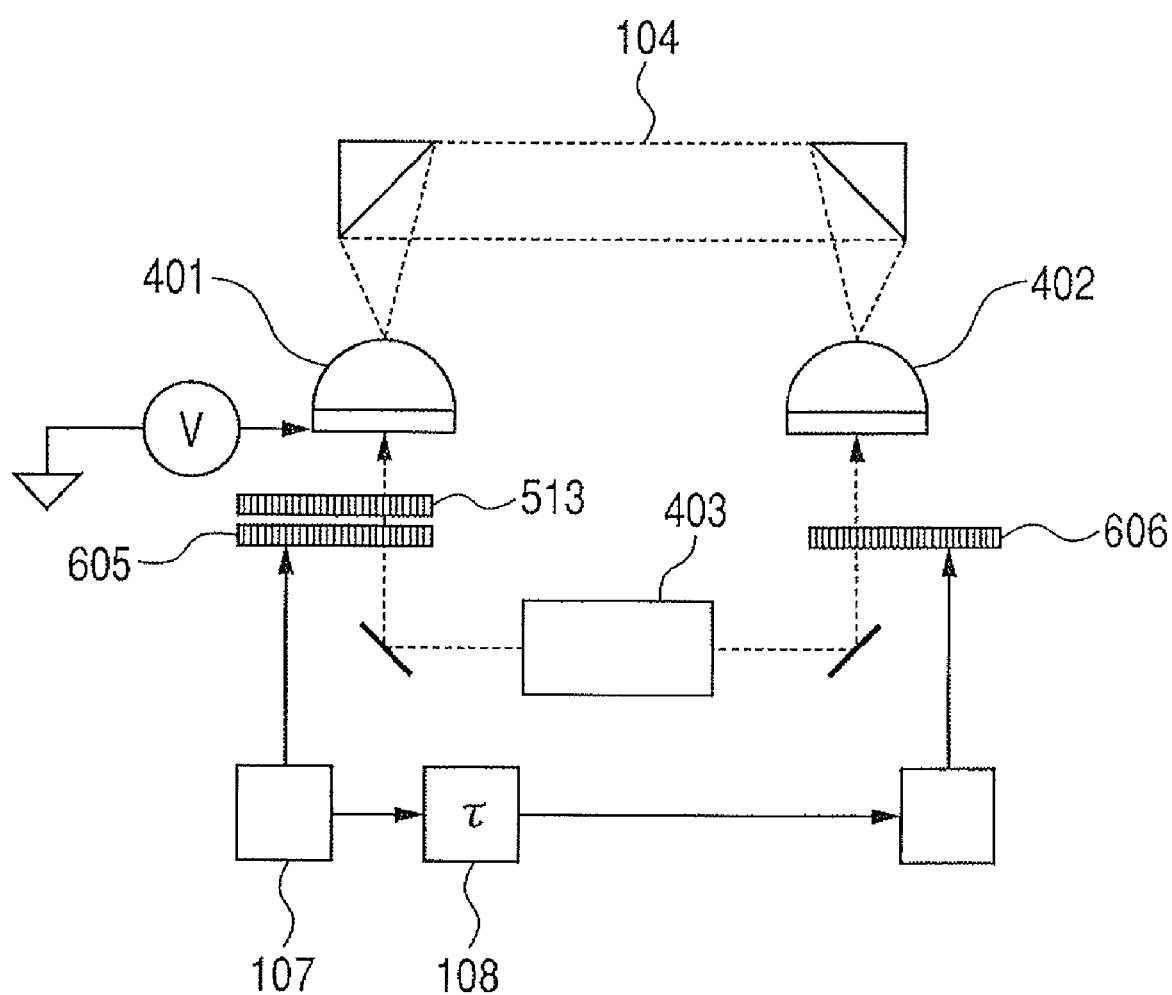
FIG. 7 illustrates schematically a constitution of Example 6 of the present invention.

FIG. 7 illustrates schematically a constitution of the apparatus and method of the analysis of this Example. In this Example, phase controller 605 is employed as band diffusing unit 105, and phase controller 606 is employed as band restoring unit 106. Phase controllers 605, 606 have the same constitution as that described in Example 5. Therefore the description thereof is omitted.

In this Example, phase controller 605, 606 control respectively the timing of introduction of the ultrashort pulsed light to generating element 401 and detecting element 402. In this operation, chopper 513 is additionally employed to control the timing of introduction of the ultrashort pulsed light nearly random at the sampling points of the terahertz wave in the same manner as in Example 4 to diffuse and restore the band.

Example 7

In this Example, the phase controllers mentioned above are modified. In the description below, the matters common to the above description are omitted.

The aforementioned phase controllers 305, 306, 605, 606 for the phase control are constituted of materials having invariable properties. In this Example, as the material for the phase control, an electro-optical element is employed which has a refractive index variable depending on an external electric field. The electro-optical element includes materials which changes the refractive index in response to the external electric field, such as BBO crystals, $LiTzO_3$ crystals, KTP crystals, and ZnTe crystals. The electro-optical element is preferably transparent to some extent to the wavelength of the light utilized.

Such a material as the phase-modulating part 310 or 610 of the phase controller enables fine adjustment of the phase to increase the freedom degree in the system control. Further, the phase controller constituted of such a material enables control of the phase state by external electric field, enabling further diffusion of the terahertz wave over a broader band range and restoration thereof. Thereby signals can be transmitted at a higher efficiency with high confidentiality. With this type of phase controller, the apparatus can readily be miniaturized since a rotation mechanism or a like mechanism is not necessary.

Example 8

In the apparatus and method of analysis in the above Examples, band-diffusing unit 105 and band-restoring unit 106 corresponding respectively to generating unit 101 and detecting unit 102 are common in the structure. For instance, in Example, 1, vibrating unit 205 and vibrating unit 206 are common in structure. However, band-diffusing unit 105 and band-restoring unit 106 may be made different in the structure by employing constitutions mentioned above. For instance, a vibrating unit and phase-controlling unit may be combinedly employed respectively as band-diffusing unit 105 and band-restoring unit 106.

Otherwise, a combination of the constitution described above (e.g., a vibrating unit and a phase-controlling unit) may be employed respectively as band-diffusing unit 105 and band-restoring unit 106. Thereby, the terahertz wave can be diffused over a broader range and restored.

Example 9

In the apparatus and method of the analysis in the above Examples, one generating unit 101 and one detecting unit 102 are provided. However, plural pairs of generating unit 101 and detecting unit 102 may be provided. With such a constitution, analysis of broader scope can be conducted in a relatively short time. For instance, plural pairs analyze different portions of the sample, or analyze the sample at different wavelength region. Plural pairs may be employed for inspecting the sample in the same wavelength region and for higher analysis accuracy by taking differential of the signals. With the plural pairs, the wavelength and the code pattern for the respective pairs may be selected suitably.

For instance, in an embodiment containing at least one pair of a band-diffusing unit and a generating unit and at least one pair of a band-restoring unit and a detecting unit, code patterns may be given to the respective pairs.

Example 10

This Example is a modification of the apparatus and method of analysis of Example 9. In this Example, the diffusion signals (coding pattern) for the respective generating units 101 are orthogonal. Thereby, crosstalk between the terahertz waves generated by the generating units 101 can readily be decreased.

Example 11

This Example 11 describes application of the above-mentioned apparatus and method of analysis to an imaging apparatus and an imaging method. Here, the matters common to the descriptions above are not explained.

In this Example, a scanning unit is provided for scanning the sample (not shown in the drawing). For instance, processing unit 109 gives a characteristic image of the sample by plotting of the responses of the terahertz wave on the scanned points or regions of the sample. Otherwise, with plural pairs of generating unit 101 and detecting unit 102, plotting of the responses of the terahertz waves on the scanned points or regions of the sample by processing unit 109 gives a characteristic image of the sample. With plural pairs of generating unit 101 and detecting unit 102 in combination with a scanning unit, the image can be obtained in a broader range in a shorter time.

In the above description, the scanning unit drives the sample, but is not limited thereto. The terahertz wave may be allowed to scan the sample with a movable optical system. Anyway, the sample or the terahertz wave is moved relatively for scanning.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-308711, filed on Nov. 15, 2006 which is hereby incorporated by reference herein in its entirety.

What is claimed is:

1. An analysis apparatus for obtaining information on a sample by utilizing a change in a propagation state of a terahertz wave, comprising:
   a generating unit for generating a terahertz wave,
   a signal-making unit for making a code pattern,
   a delaying unit for delaying the code pattern produced by the signal-making unit,
   a band-diffusing unit for diffusing a band of the terahertz wave by modulating the phase of the terahertz wave generated by the generating unit in accordance with the code pattern produced by the signal-making unit,
   a detecting unit for detecting the terahertz wave, and
   a band-restoring unit for restoring the band by modulating the phase of the terahertz wave in accordance with the code pattern being output from the delaying unit before detection by the detecting unit.

2. The analysis apparatus according to claim 1, wherein at least one pair of the band-diffusing unit and the generating unit, and at least one pair of the band-restoring unit and the detecting unit which pairs correspond to each other are provided.

3. The analysis apparatus according to claim 1, wherein at least one of the band-diffusing unit and the band-restoring unit vibrates mechanically the generating unit or the detecting unit in the direction of propagation of the terahertz to modulate the phase of the terahertz wave.

4. The analysis apparatus according to claim 1, wherein at least one of the band-diffusing unit and the band-restoring unit controls timing of generation or detection of the terahertz wave in the generating unit of the detecting unit by utilizing controlling light to modulate the phase of the terahertz wave.

5. The analysis apparatus according to claim 4, wherein at least one of the band-diffusing unit and the band-restoring unit has a delaying optical unit for controlling the incident timing of the control light for triggering the generation or detection of the terahertz wave in the generating unit or the detecting unit, and a vibrating unit for vibrating mechanically the delaying optical unit.

6. The analysis apparatus according to claim 4, wherein at least one of the band-diffusing unit and the band-restoring unit has a phase controller for controlling the phase of the terahertz wave propagating or the incident timing of the controlling light to the generating unit or the detecting unit.

7. The analysis apparatus according to claim 4, wherein the apparatus further comprises a chopper for modulating the intensity of the controlling light.

8. The analysis apparatus according to claim 1, wherein at least one of the band-diffusing unit and the band-restoring unit controls the phase of the propagating terahertz wave to modulate the phase of the terahertz wave.

9. The analysis apparatus according to claim 1, wherein the apparatus further comprises a means for imaging characteristics of the sample by placing signals obtained in the detecting unit in the manner of making the signals correspond to points irradiated with the terahertz wave.

10. An analysis method for obtaining information on a sample by utilizing a change in propagation state of a terahertz wave, comprising the steps of:
    generating a terahertz wave,
    diffusing a band of the terahertz wave by modulating the phase of the terahertz wave in accordance with a code pattern,
    irradiating the sample with the terahertz wave having a diffused band obtained in the diffusing step, detecting the terahertz wave as a result of the irradiating step,
    band-restoring the band by modulating the phase of the terahertz wave before the detecting step in accordance with the code-pattern, and
    delaying the code-pattern to adjust the timing of restoration of the band in the band-restoring step.

11. The analysis method according to claim 10, wherein the method comprises further a step of imaging characteristics of the sample by placing signals obtained in the detecting step in the manner of making the signals correspond to points irradiated with the terahertz wave.

* * * * *